(12) United States Patent
Paillaman et al.

(10) Patent No.: US 6,625,244 B2
(45) Date of Patent: Sep. 23, 2003

(54) INSPECTION APPARATUS FOR EXAMINING JET PUMP BEAMS IN NUCLEAR REACTORS

(75) Inventors: Rodolfo Paillaman, Huntersville, NC (US); Trevor Davis, Charlotte, NC (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 10/060,611

(22) Filed: Jan. 30, 2002

(65) Prior Publication Data

US 2003/0142777 A1 Jul. 31, 2003

(51) Int. Cl.⁷ .............................................. G21C 17/00
(52) U.S. Cl. ........................ 376/245; 376/249; 376/252
(58) Field of Search ................................ 376/245, 249, 376/252; 73/622, 624, 625, 627, 628; 417/63

(56) References Cited

U.S. PATENT DOCUMENTS

| | | | |
|---|---|---|---|
| 4,394,345 A | | 7/1983 | De Briere et al. |
| 4,531,663 A | * | 7/1985 | Kajiyama et al. ........... 376/249 |
| 5,194,215 A | * | 3/1993 | Nachbar et al. ............ 376/245 |
| 5,568,527 A | * | 10/1996 | Richardson et al. ........ 376/245 |
| 5,710,378 A | | 1/1998 | Dykes et al. |
| 5,864,595 A | * | 1/1999 | Burrows et al. ............ 376/249 |
| 6,137,853 A | * | 10/2000 | Duckering et al. ......... 376/252 |

FOREIGN PATENT DOCUMENTS

| JP | 57053657 | * | 3/1982 | ................. 376/245 |
|---|---|---|---|---|

* cited by examiner

Primary Examiner—Michael J. Carone
Assistant Examiner—Daniel Matz
(74) Attorney, Agent, or Firm—Armstrong Teasdale LLP

(57) ABSTRACT

An inspection apparatus for inspecting jet pump beams of nuclear reactors is provided. The inspection apparatus includes a base straddlingly mountable on a jet pump beam. The base includes a beam bolt opening sized to receive a jet pump beam bolt. A first transducer holder is coupled to a first side portion of the base, and a second transducer holder coupled to a second side portion of the base. The first side portion is opposed to the second side portion. Each holder includes an adjustment cylinder configured to contact the jet pump beam when activated.

25 Claims, 5 Drawing Sheets

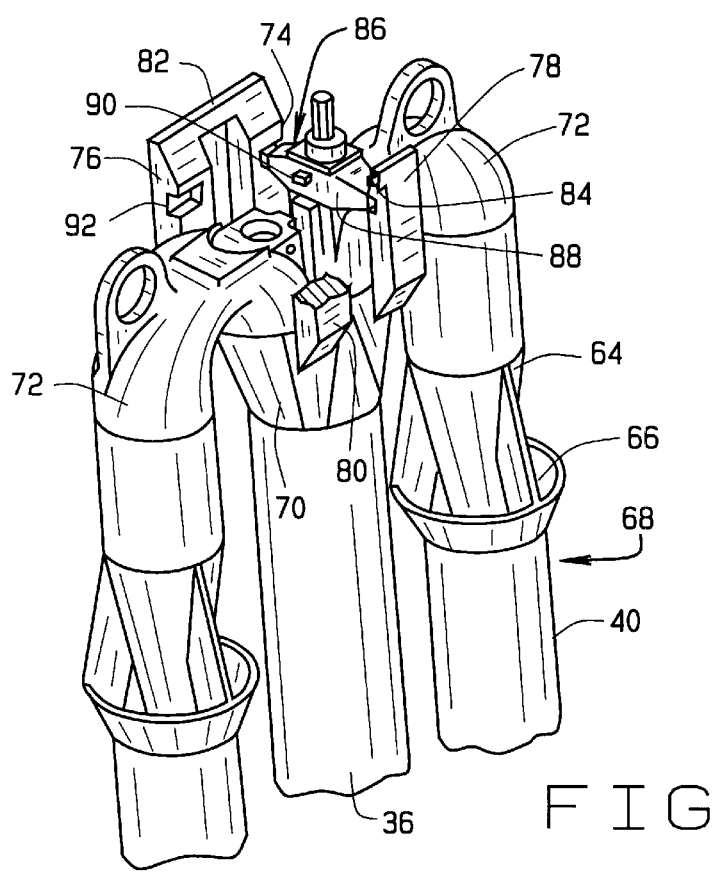

INSPECTION APPARATUS FOR EXAMINING JET PUMP BEAMS IN NUCLEAR REACTORS

BACKGROUND OF THE INVENTION

This invention relates generally to inspection of nuclear reactors, and more particularly to ultrasonic examination of jet pump beams within a nuclear reactor pressure vessel.

A reactor pressure vessel (RPV) of a boiling water reactor (BWR) typically has a generally cylindrical shape and is closed at both ends, e.g., by a bottom head and a removable top head. A top guide typically is spaced above a core plate within the RPV. A core shroud, or shroud, typically surrounds the core and is supported by a shroud support structure. Particularly, the shroud has a generally cylindrical shape and surrounds both the core plate and the top guide. There is a space or annulus located between the cylindrical reactor pressure vessel and the cylindrically shaped shroud.

In a BWR, hollow tubular jet pumps positioned within the shroud annulus provide the required reactor core water flow. The upper portion of the jet pump, known as the inlet mixer, is laterally positioned and supported against two opposing rigid contacts within restrainer brackets by a gravity actuated wedge. The inlet mixers are each held in place at the top end by a preloaded beam. To secure the assembly, the jet pump beam is assembled with a high preload, applied by installing the jet pump beam bolt with a hydraulic tensioner.

The static and dynamic loads on jet pump beams including vibrations imposed during reactor operation have been found to cause, in some instances, beam cracking that begins in the upper central portion of the beams. Each jet pump beam holds in place a pipe elbow, which leads reactor water from an inlet riser pipe toward a jet pump nozzle.

Cracking in a jet pump beam threatens the release of a pipe elbow from its normal position, which could impair proper jet pump operation. Accordingly, it is desirable to determine the physical integrity of jet pump beams on a regular basis, as for example by ultrasonic examination. In some cases, this is done by dismantling the jet pump beams from the reactor and transporting them to a laboratory for testing. In other cases, an ultrasonic on-site inspection of the jet pump beams within the reactor vessel is performed.

BRIEF DESCRIPTION OF THE INVENTION

In one aspect, an inspection apparatus for inspecting jet pump beams of nuclear reactors is provided. The nuclear reactor includes at least one jet pump with each jet pump having a jet pump beam and a jet pump beam bolt. The inspection apparatus includes a base straddlingly mountable on a jet pump beam. The base includes a beam bolt opening sized to receive a jet pump beam bolt. A first transducer holder is coupled to a first side portion of the base, and a second transducer holder coupled to a second side portion of the base. The first side portion is opposed to the second side portion. Each holder includes an adjustment cylinder configured to contact the jet pump beam when activated.

In another aspect, a method of inspecting a jet pump beam in a nuclear reactor is provided. The nuclear reactor includes at least one jet pump with each jet pump having a jet pump beam and a jet pump beam bolt. The method includes mounting an inspection apparatus on a jet pump beam, and scanning the jet pump beam with the inspection apparatus. The inspection apparatus includes a base straddlingly mountable on a jet pump beam. The base includes a beam bolt opening sized to receive a jet pump beam bolt. A first transducer holder is coupled to a first side portion of the base, and a second transducer holder coupled to a second side portion of the base. The first side portion is opposed to the second side portion. Each holder includes an adjustment cylinder configured to contact the jet pump beam when activated.

BRIEF DESCRIPTION OF THE DRAWINGS

FIG. 2 is a perspective view, with parts cut away, of a jet pump assembly shown in FIG. 1.

FIG. 3 is a side view of the jet pump beam shown in FIG. 2.

DETAILED DESCRIPTION OF THE INVENTION

An inspection apparatus that performs volumetric and surface examinations of jet pump beams is described below in more detail. The inspection apparatus examines the arm regions of the jet pump beam with self adjusting immersion ultrasonic transducers and examines the bore-hole region of the jet pump beam with opposed ultrasonic transducers which can be operated in a "pitch-catch" mode. The inspection apparatus permits on-site inspection of jet pump beams within the reactor without dismantling the jet pumps.

Figure 1:
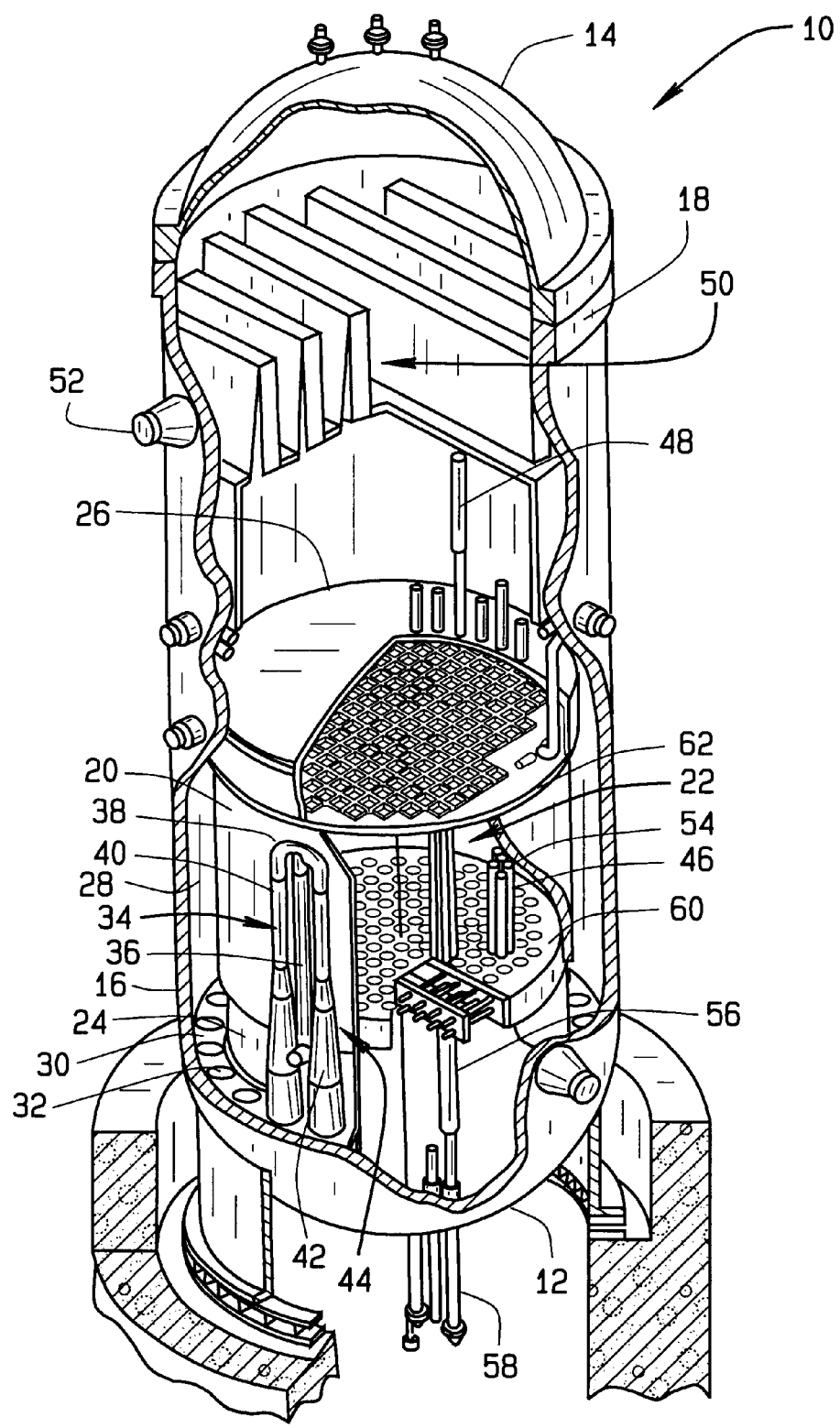
FIG. 1 is a sectional view, with parts cut away, of a boiling water nuclear reactor pressure vessel.

Referring now to the figures, FIG. 1 is a sectional view, with parts cut away, of a boiling water nuclear reactor pressure vessel (RPV) 10. RPV 10 has a generally cylindrical shape and is closed at one end by a bottom head 12 and at its other end by a removable top head 14. A side wall 16 extends from bottom head 12 to top head 14. Side wall 16 includes a top flange 18. Top head 14 is attached to top flange 18. A cylindrically shaped core shroud 20 surrounds a reactor core 22. Shroud 20 is supported at one end by a shroud support 24 and includes a removable shroud head 26 at the other end. An annulus 28 is formed between shroud 20 and side wall 16. A pump deck 30, which has a ring shape, extends between shroud support 24 and RPV side wall 16. Pump deck 30 includes a plurality of circular openings 32, with each opening housing a jet pump 34. Jet pumps 34 are circumferentially distributed around core shroud 20. An inlet riser pipe 36 is coupled to two jet pumps 34 by a transition assembly 38. Each jet pump 34 includes an inlet mixer 40, and a diffuser 42. Inlet riser 36 and two connected jet pumps 34 form a jet pump assembly 44.

Heat is generated within core 22, which includes fuel bundles 46 of fissionable material. Water circulated up through core 22 is at least partially converted to steam. Steam separators 48 separates steam from water, which is recirculated. Residual water is removed from the steam by steam dryers 50. The steam exits RPV 10 through a steam outlet 52 near vessel top head 14.

The amount of heat generated in core 22 is regulated by inserting and withdrawing control rods 54 of neutron absorbing material, such as for example, hafnium. To the extent that control rod 54 is inserted into fuel bundle 46, it absorbs neutrons that would otherwise be available to promote the chain reaction which generates heat in core 22. Control rod guide tubes 56 maintain the vertical motion of control rods 54 during insertion and withdrawal. Control rod drives 58 effect the insertion and withdrawal of control rods 54. Control rod drives 58 extend through bottom head 12.

Fuel bundles 46 are aligned by a core plate 60 located at the base of core 22. A top guide 62 aligns fuel bundles 46 as they are lowered into core 22. Core plate 60 and top guide 62 are supported by core shroud 20.

FIG. 2 is a perspective view, with parts cut away, of jet pump assembly 44. Jet pump assembly 44 includes riser pipe 36 coupled to a pair of jet pumps 34 by transition assembly 38. Each jet pump 34 includes a jet pump nozzle 64, a suction inlet 66, an inlet mixer 40, and a diffuser 42 (shown in FIG. 1). Jet pump nozzle 64 is positioned in suction inlet 66 which is located at a first end 68 of inlet mixer 40.

Transition assembly 38 includes a base piece 70 and two elbows 72. Each elbow 72 is coupled to a jet pump nozzle 64. Support arms 74, 76, 78, and 80 extend from transition assembly base piece 70. Cross beam 82 connects support arms 74 and 76, and cross beam 84 (partially cut away in FIG. 2) connects support arms 78 and 80. A jet pump beam 86 extends between support arms 74 and 78. An identical jet pump beam (not shown) extends between support arms 76 and 80. Referring also to FIG. 3, jet pump beam 86 includes a raised central portion 88 and trunions 90. The ends of jet pump beam 86 are supported in notches 92 located in support beams 74 and 78. A beam bolt 94 includes a multisided head 96, a threaded portion 98, and a butt end 100 including a lower bearing surface 102 which bears against a disc 104 seated in a counter bore 105 of elbow 72. Beam bolt 94 threadedly engages a threaded bolt opening 106 in jet pump beam 86.

A locking assembly 110 prevents beam bolt 94 from loosening. Locking assembly 110 includes a locking sleeve 112 and a lock plate 114. Locking sleeve 112 includes a base portion 116 at a first end 118 and a bore 120 extending from first end 118 to a second end 122. Bore 120 is sized and shaped to matingly receive beam bolt head 96.

Figure 4:
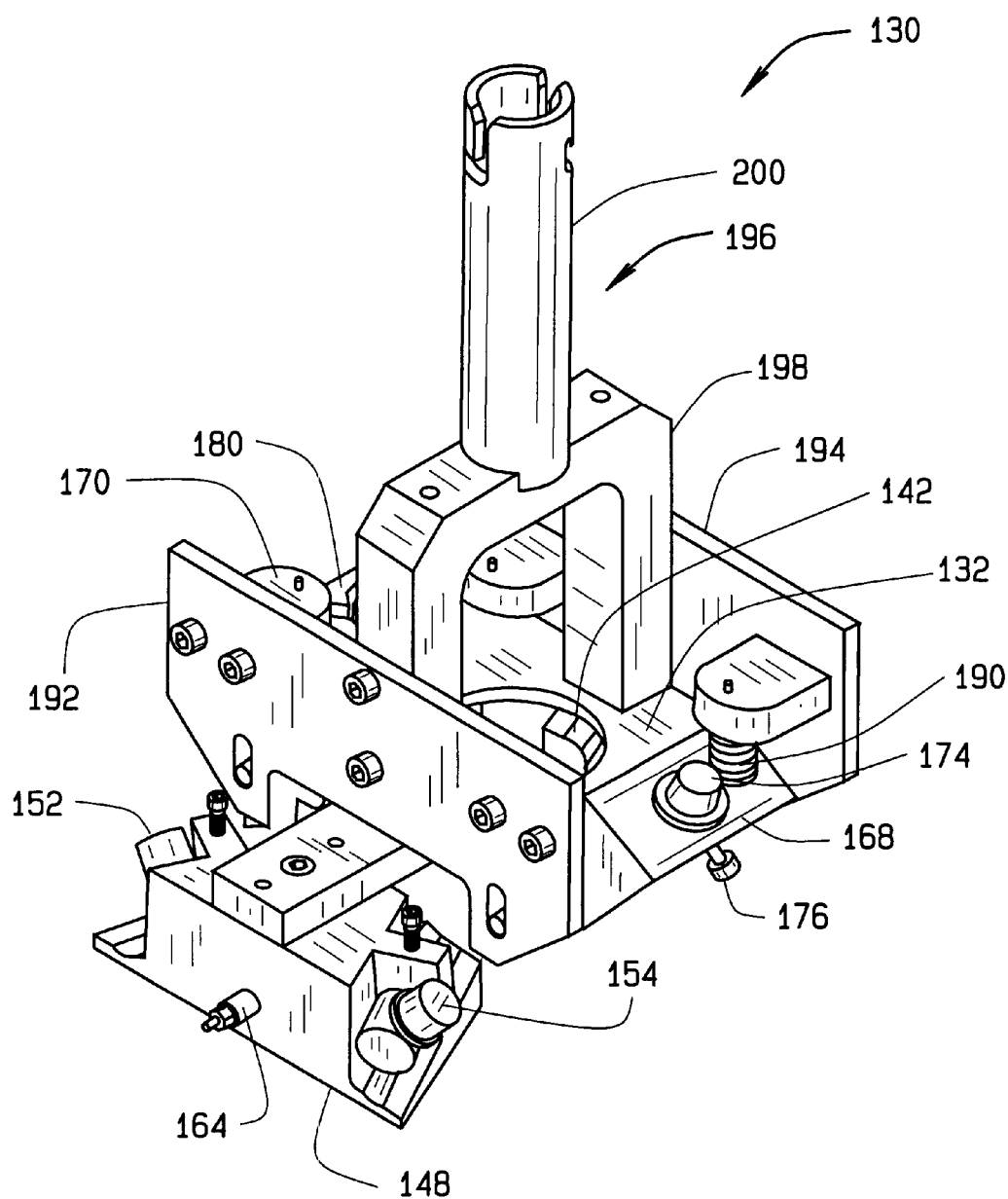
FIG. 4 is a perspective view of an inspection apparatus in accordance with an embodiment of the present invention.
Figure 5:
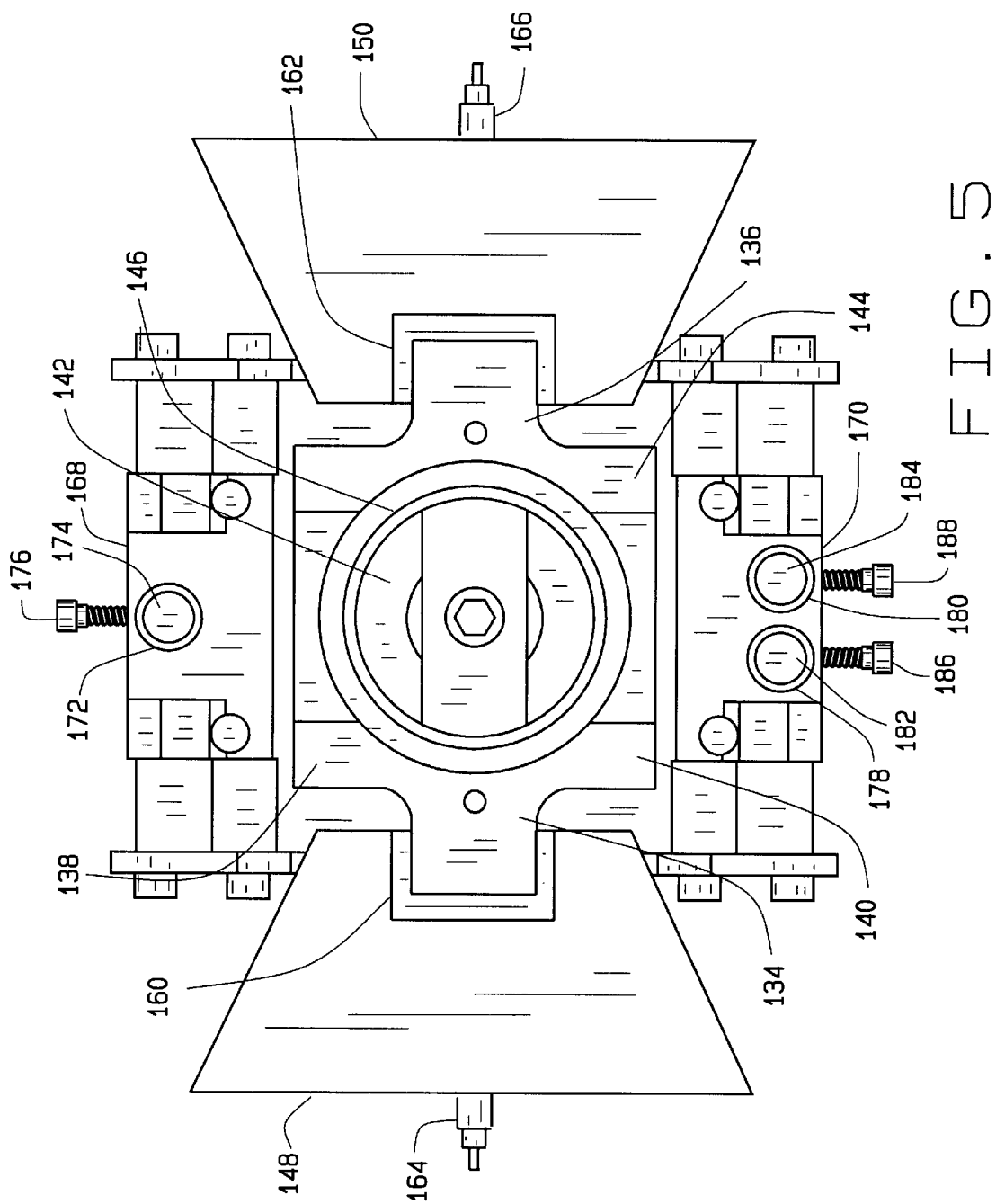
FIG. 5 is a bottom view of the inspection apparatus shown in FIG. 4.
Figure 6:
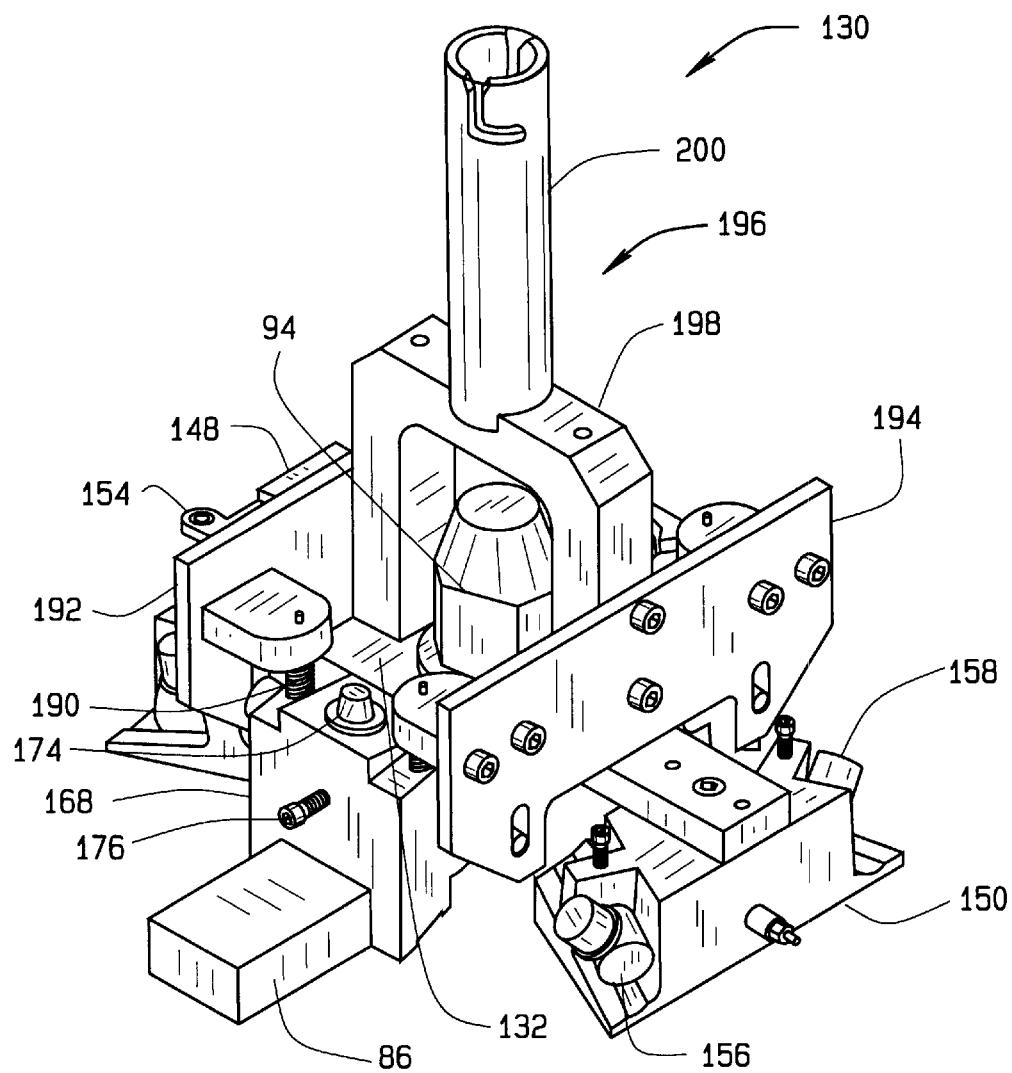
FIG. 6 is a perspective view of the inspection apparatus shown in FIG. 4 mounted on a jet pump beam.

FIG. 4 is a perspective view of an inspection apparatus 130 in accordance with an exemplary embodiment of the present invention, FIG. 5 is a bottom view of inspection apparatus 130, and FIG. 6 is a perspective view of the inspection apparatus 130 mounted on jet pump beam 86. Referring to FIGS. 4, 5, and 6, inspection apparatus 130 includes a base 132 having opposing first and second side portions 134 and 136, and opposing third and fourth side portions 138 and 140. A beam bolt opening 142 extends through base 132. Bolt opening 142 is sized to receive jet pump beam bolt 94 and a bottom surface 144 of base 132 includes a seat 146 sized to receive locking sleeve 112 and locking plate 114 so that base 132 is straddlingly mountable on beam 86.

A first transducer holder 148 is coupled to first side portion 134 of base 132 and a second transducer holder 150 is coupled to second side portion 136 of base 132. Ultrasonic transducers 152 and 154 are mounted in first holder 148 and ultrasonic transducers 156 and 158 are mounted in second holder 150. Transducers 152, 154, 156, and 158 are mounded in holders 148 and 150 so that the transducers mounted in first holder 148 are opposed to the transducers mounted in second holder 150. Particularly, transducer 152 opposes transducer 158 and transducer 154 opposes transducer 156. This arrangement permits operation in a "pitch-catch" mode where one transducer sends ultrasonic signals and the opposed transducer receives a portion of the signals.

First holder 148 includes a recessed portion 160 and second holder 150 includes a recessed portion 162. Recessed portions 160 and 162 are sized to receive jet pump beam trunions 90 when base 130 is mounted on beam 86. First holder 148 and second holder 150 include pneumatic adjustment cylinders 164 and 166 respectively. When adjustment cylinders 164 and 166 are activated, they extend into recessed portions 160 and 162 respectively to engage trunions 90 which secures apparatus 130 to beam 86 and prevents apparatus 130 from rocking during the scanning operation. In an alternate embodiment, adjustment cylinders 164 and 166 are hydraulic cylinders.

A first mounting member 168 is pivotally coupled to third side portion 138 and a second mounting member 170 is pivotally coupled to fourth side member 140. A bore 172 extends through first mounting member 168. Bore 172 is sized to receive an immersion ultrasonic transducer 174. A set screw 176 secures transducer 174 in place in bore 172. Two bores 178 and 180 extend through second mounting member 170. Bores 178 and 180 are sized to receive immersion ultrasonic transducers 182 and 184 respectively. Set screws 186 and 188 secure transducers 182 and 184 in place in bores 178 and 180 respectively. The pivoting movement of mounting members 168 and 170 permits self adjustment and proper alignment of immersion ultrasonic transducers 174, 182 and 184. Particularly, positioning springs 190 impart a downward force on mounting members 168 and 170 to keep mounting members 168 and 170 in contact with beam 86 and thus keep transducers 174, 182, and 184 a predetermined distance from beam 86 and in proper alignment with beam 86. Positioning springs 190 are attached to brackets 192 and 194 coupled to first and second side portions 134 and 136 of base 132.

A lifting member 196 is coupled to base 132. Lifting member 196 includes a U-shaped bale 198 coupled to base 132 and a connector member 200 extending from bale 198. Connector member 200 is configured to connect to the end connector of a handling pole (not shown). In other embodiments, connector member is configured to connect to ropes, a crane, or an automatic tool manipulator.

In operation, inspection apparatus 130 is lowered onto jet pump beam 86 using a service pole (not shown), or any other suitable lifting means, coupled to lifting member 196. Apparatus 130 is positioned on beam 86 so that beam bolt 94 is received in bolt opening 106 and lock plate 114 mates with seat 146. As apparatus 130 is positioned on beam 86, mounting members 168 and 170 make contact with the arms of beam 86 which causes mounting members 168 and 170 to pivot so that immersion ultrasonic transducers 174, 182, and 184 into proper alignment with beam 86. Adjustment cylinders 164 and 166 are then activated which clamps apparatus 130 to beam 86 to prevent rocking during scanning. Beam 86 is then scanned using ultrasonic transducers 152, 154, 156, and 158, and immersion ultrasonic transducers 174, 182, and 184. When the scanning is completed, alignment cylinders are deactivated and apparatus 130 is lifted off beam 86.

While the invention has been described in terms of various specific embodiments, those skilled in the art will recognize that the invention can be practiced with modification within the spirit and scope of the claims.

What is claimed is:

1. An inspection apparatus for inspecting jet pump beams of a nuclear reactor, the nuclear reactor comprising at least one jet pump with each jet pump comprising a jet pump beam and a jet pump beam bolt, said inspection apparatus comprising:

a base straddlingly mountable on a jet pump beam, said base comprising a beam bolt opening sized to receive a jet pump beam bolt;

a first transducer holder coupled to a first side portion of said base; and a second transducer holder coupled to a second side portion of said base, said first side portion opposite to said second side portion, each said holder comprising an adjustment cylinder, said adjustment cylinder configured to contact the jet pump beam when activated.

2. An inspection apparatus in accordance with claim 1 wherein each transducer holder comprises at least one ultrasonic transducer positioned to examine the jet pump beam.

3. An inspection apparatus in accordance with claim 2 wherein each transducer holder comprises two ultrasonic transducers positioned to examine the jet pump beam so that said ultrasonic transducers of said first transducer holder are oppositely disposed to said ultrasonic transducers of said second transducer holder.

4. An inspection apparatus in accordance with claim 1 further comprising at least one immersion ultrasonic transducer pivotally mounted to a third side portion of said base and at least one immersion ultrasonic transducer pivotally mounted to a fourth side portion of said base.

5. An inspection apparatus in accordance with claim 4 comprising one immersion ultrasonic transducer pivotally mounted to said third side portion and two immersion ultrasonic transducers pivotally mounted to said fourth side portion.

6. An inspection apparatus in accordance with claim 4 further comprising a first mounting member pivotally coupled to said third side portion of said base and a second mounting member pivotally coupled to said fourth side portion of said base.

7. An inspection apparatus in accordance with claim 6 wherein each said mounting member comprises at least one bore extending therethrough, each said bore sized to receive an immersion ultrasonic transducer.

8. An inspection apparatus in accordance with claim 1 further comprising a lift member coupled to said base, said lift member configured to couple to a lifting means.

9. An inspection apparatus in accordance with claim 1 wherein said adjustment cylinder comprises a pneumatic adjustment cylinder.

10. A method of inspecting a jet pump beam in a nuclear reactor, the reactor comprising at least one jet pump with each jet pump comprising a jet pump beam and a jet pump beam bolt, said method comprising:

mounting an inspection apparatus on a jet pump beam; and scanning the jet pump beam with the inspection apparatus;

said inspection apparatus comprising:

a base straddlingly mountable on the jet pump beam, the base comprising a beam bolt opening sized to receive the jet pump beam bolt;

a first transducer holder coupled to a first side portion of the base; and a second transducer holder coupled to a second side portion of the base, the first side portion opposed to the second side portion, each said holder comprising an adjustment cylinder, said adjustment cylinder configured to contact the jet pump beam when activated.

11. A method in accordance with claim 10 wherein mounting an inspection apparatus on a jet pump beam comprises:

positioning the inspection apparatus on the beam so that the beam bolt is received in the bolt opening of the inspection apparatus base; and activating the adjustment cylinders to contact the jet pump beam to prevent the inspection apparatus from rocking during the scanning step.

12. A method in accordance with claim 10 wherein each transducer holder comprises at least one ultrasonic transducer positioned to scan the jet pump beam.

13. A method in accordance with claim 12 wherein each transducer holder comprises two ultrasonic transducers positioned to scan the jet pump beam so that the ultrasonic transducers of the first transducer holder are oppositely disposed to the ultrasonic transducers of the second transducer holder.

14. A method in accordance with claim 10 wherein the inspection apparatus further comprises at least one immersion ultrasonic transducer pivotally mounted to a third side portion of the base and at least one immersion ultrasonic transducer pivotally mounted to a fourth side portion of the base.

15. A method in accordance with claim 14 wherein the inspection apparatus comprises one immersion ultrasonic transducer pivotally mounted to the third side portion and two immersion ultrasonic transducers pivotally mounted to the fourth side portion.

16. A method in accordance with claim 14 wherein the inspection apparatus further comprises a first mounting member pivotally coupled to the third side portion of the base and a second mounting member pivotally coupled to the fourth side portion of the base.

17. A method in accordance with claim 16 wherein each mounting member comprises at least one bore extending therethrough, each bore sized to receive an immersion ultrasonic transducer.

18. A method in accordance with claim 10 wherein the inspection apparatus further comprises a lift member coupled to the base, the lift member configured to couple to a lifting means.

19. A method in accordance with claim 10 wherein each adjustment cylinder comprises a pneumatic adjustment cylinder.

20. An inspection apparatus for inspecting jet pump beams of a nuclear reactor, the nuclear reactor comprising at least one jet pump with each jet pump comprising a jet pump beam, a jet pump beam bolt, and a beam lock assembly, the beam locking assembly comprising a locking sleeve and a lock plate, said inspection apparatus comprising:

a base mountable on a jet pump beam, said base comprising a beam bolt opening sized to receive the jet pump beam bolt, said beam bolt opening comprising a recessed portion sized to receive the locking sleeve to permit said inspection apparatus to sit flat on the lock plate;

a first transducer holder coupled to a first side portion of said base; and a second transducer holder coupled to a second side portion of said base, said first side portion opposite to said second side portion, each said holder comprising an adjustment cylinder, said adjustment cylinder configured to contact the jet pump beam when activated.

21. An inspection apparatus in accordance with claim 20 wherein each said transducer holder comprises two ultrasonic transducers positioned to examine the jet pump beam so that said ultrasonic transducers of said first transducer holder are oppositely disposed to said ultrasonic transducers of said second transducer holder.

22. An inspection apparatus in accordance with claim 20 further comprising at least one immersion ultrasonic transducer pivotally mounted to a third side portion of said base and at least one immersion ultrasonic transducer pivotally mounted to a fourth side portion of said base.

23. An inspection apparatus in accordance with claim 22 comprising one immersion ultrasonic transducer pivotally mounted to said third side portion and two immersion ultrasonic transducers pivotally mounted to said fourth side portion.

24. An inspection apparatus in accordance with claim 22 further comprising a first mounting member pivotally coupled to said third side portion of said base and a second mounting member pivotally coupled to said fourth side portion of said base.

25. An inspection apparatus in accordance with claim 24 wherein each said mounting member comprises at least one bore extending therethrough, each said bore sized to receive an immersion ultrasonic transducer.

* * * * *